United States Patent [19]

Molnar-Kimber et al.

[11] Patent Number: 5,504,091
[45] Date of Patent: Apr. 2, 1996

[54] BIOTIN ESTERS OF RAPAMYCIN

[75] Inventors: Katherine L. Molnar-Kimber, Glenside, Pa.; Timothy D. Ocain, Waltham, Mass.; Steven K. Vernon, Havertown, Pa.; John J. Huang, San Carlos, Calif.

[73] Assignee: American Home Products Corporation, Madison, N.J.

[21] Appl. No.: 224,206

[22] Filed: Apr. 14, 1994

Related U.S. Application Data

[63] Continuation-in-part of Ser. No. 54,654, Apr. 23, 1993, abandoned.

[51] Int. Cl.$^6$ ........................ C07D 519/00; A61K 31/395
[52] U.S. Cl. ........................ 514/291; 540/456; 435/7.1; 435/975; 436/547; 436/92
[58] Field of Search ........................ 540/456; 514/291

[56] References Cited

U.S. PATENT DOCUMENTS 3,929,992  12/1975  Sehgal et al. ........................ 514/291

(List continued on next page.)

FOREIGN PATENT DOCUMENTS

283801A2  3/1988  European Pat. Off. ........................ 514/291

(List continued on next page.)

OTHER PUBLICATIONS

Venzina, C., J. Antibiot. 28:721 (1975).

(List continued on next page.)

*Primary Examiner*—Robert T. Bond
*Attorney, Agent, or Firm*—Arnold S. Milowsky

[57] ABSTRACT

A compound of the structure $R^1$ and $R^2$ are each, independently, hydrogen or

[structure shown]

X is $$-\overset{O}{\underset{\|}{C}}-(CH_2)_m-CHR^3-(CH_2)_n NR^4-;$$

Y is $$-\overset{O}{\underset{\|}{C}}-(CH_2)_p-Z-(CH_2)_q NH-;$$

Z is $-CH_2-$, $-S-S-$, or

[structure shown]

$R^3$ is hydrogen, alkyl, arylalkyl, alkenyl, alkynyl, $-(CH_2)_q CO_2 R^5$, $-(CH_2)_r NR^6 R^7$, carbamylalkyl, aminoalkyl, hydroxyalkyl, guanylalkyl, mercaptoalkyl, alkylthioalkyl, indolylmethyl, hydroxyphenylmethyl, imidazoylmethyl, halo, trifluoromethyl, or phenyl which is optionally mono-, di-, or tri-substituted;

$R^4$, $R^6$, and $R^7$ are each, independently, hydrogen, alkyl, or arylalkyl;

$R^5$ is hydrogen, alkyl, arylalkyl, alkenyl, alkynyl, or phenyl which is optionally mono-, di-, or tri-substituted;

h=0–1;
j=0–1;
m=0–6;
n=0–6;
p=0–10;
q=0–10;
r=0–6;

with the proviso that $R^1$ and $R^2$ are not both hydrogen, or a pharmaceutically acceptable salt thereof which is useful for inducing immunosuppression; in the treatment of transplantation rejection, host vs. graft disease, autoimmune diseases, diseases of inflammation, solid tumors, fungal infections, adult T-cell leukemia/lymphoma, and hyperproliferative vascular disorders; for measuring levels of rapamycin; for isolating rapamycin-binding proteins; and detecting monoclonal antibodies specific for rapamycin or derivatives thereof.

7 Claims, No Drawings

U.S. PATENT DOCUMENTS

| | | |
|---|---|---|
| 3,993,749 | 11/1976 | Sehgal et al. ............... 514/291 |
| 4,316,885 | 2/1982 | Rakhit ....................... 514/291 |
| 4,401,653 | 8/1983 | Eng .......................... 514/291 |
| 4,650,803 | 3/1987 | Stella et al. ................. 514/291 |
| 4,885,171 | 12/1989 | Surendra et al. ............ 514/291 |
| 5,078,999 | 1/1992 | Warner et al. .............. 514/291 |
| 5,080,899 | 1/1992 | Sturm et al. ................ 514/291 |
| 5,089,390 | 2/1992 | Davalian et al. ............ 514/291 |
| 5,091,389 | 2/1992 | Ondeyka et al. ............ 514/291 |
| 5,100,883 | 3/1992 | Schiehser ................... 514/291 |
| 5,100,899 | 3/1992 | Calne ........................ 514/291 |
| 5,102,876 | 4/1992 | Caufield et al. ............. 514/291 |
| 5,118,677 | 6/1992 | Caufield ..................... 514/291 |
| 5,118,678 | 6/1992 | Kao et al. ................... 514/291 |
| 5,120,842 | 6/1992 | Failli et al. ................. 514/291 |
| 5,130,307 | 7/1992 | Failli et al. ................. 514/291 |
| 5,138,051 | 8/1992 | Hughes et al. .............. 514/291 |
| 5,151,413 | 9/1992 | Caufield et al. ............. 514/291 |
| 5,169,851 | 12/1992 | Hughes et al. .............. 514/291 |
| 5,177,203 | 1/1993 | Failli et al. ................. 514/291 |
| 5,194,447 | 3/1993 | Kao .......................... 514/291 |

FOREIGN PATENT DOCUMENTS

| | | | |
|---|---|---|---|
| 473961A2 | 8/1991 | European Pat. Off. | 514/291 |
| 507555A1 | 3/1992 | European Pat. Off. | 514/291 |
| 506032A1 | 3/1992 | European Pat. Off. | 514/291 |
| 525960A1 | 6/1992 | European Pat. Off. | 514/291 |
| WO9008957 | 8/1990 | WIPO | 514/291 |
| WO9222332 | 12/1992 | WIPO | 514/291 |
| WO9325533 | 12/1993 | WIPO | 514/291 |

OTHER PUBLICATIONS

Sehgal, S. N., J. Antibiot. 28:727 (1975).

Baker, H. J., Antibiot. 31:539 (1978).

Martel, R. R., Can. J. Physiol. Pharmacol. 55:48 (1977).

Staruch, M. J., FASEB 3:3411 (1989).

Dumont, F. J., FASEB 3:5256 (1989).

Calne, R. Y., Lancet 1183 (1978).

Morris, R. E., Med. Sci. Res. 17:877 (1989).

Baeder, W. L. Fifth Int. Conf. Inflamm. Res. Assoc. 121 (Abstract) (1990).

Meiser, B. M., J. Heart Lung Transplant 11 (pt 2):197 (1992).

Meiser, B. M., J. Heart Lung Transplant 9: 55 (1992).

Stepkowski, S. M., Transplantation Proceedings 23(1): 507–508 (1991).

BIOTIN ESTERS OF RAPAMYCIN

CROSS REFERENCE TO RELATED APPLICATION

This application is a continuation-in-pan application of Ser. No. 08/054,654, filed Apr. 23, 1993, now abandoned.

BACKGROUND OF THE INVENTION

This invention relates to biotin derivatives of rapamycin and a method for using them for inducing immunosuppression; in the treatment of transplantation rejection, host vs. graft disease, autoimmune diseases, diseases of inflammation, solid tumors, fungal infections, adult T-cell leukemia/lymphoma, and hyperproliferative vascular disorders; for measuring levels of rapamycin; for isolating rapamycin-binding proteins; and detecting monoclonal antibodies specific for rapamycin or derivatives thereof.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. Nos. 3,929,992; and 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], adult T-cell leukemia/lymphoma [European Patent Application 525,960 A1], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions. U.S. Pat. No. 5,100,883 discloses fluorinated esters of rapamycin. U.S. Pat. No. 5,118,677 discloses amide esters of rapamycin. U.S. Pat. No. 5,118,678 discloses carbamates of rapamycin. U.S. Pat. No. 5,130,307 discloses aminoesters of rapamycin. U.S. Pat. No. 4,650,803 discloses aminoacyl esters of rapamycin. U.S. Pat. No. 5,177,203 discloses sulfonates and sulfamates of rapamycin. U.S. Pat. No. 5,194,447 discloses sulfonylcarbamates of rapamycin. PCT Publication WO 92/05179 discloses carboxylic acid esters of rapamycin.

Yatscoff has reported that rapamycin levels can be quantitated using HPLC method with a sensitivity of 1 ng/ml [Ther. Drug Monitoring 14: 138 (1992)] This method is time consuming and each sample must be assayed individually.

Immunoassays have been developed for numerous proteins as well as various drugs including cyclosporin A [Morris, R. G., Ther. Drug Monitoring 14: 226(1992)], and FK506 [Tamura, Transplant Proc. 19: 23 (1987); Cadoff, Transplant Proc. 22: 50 (1990)]. Numerous types of immunoassays, that have been developed to measure proteins or compounds, have been based on competitive inhibition, dual antibodies, receptor-antibody interactions, antigen capture, dipstick, antibody or receptor trapping, or on affinity chromatography. Affinity columns with rapamycin have been reported in which a rapamycin analog was covalently attached to a matrix [Fretz J. Am. Chem. Soc. 113: 1409 (1991)]. These columns have been used to isolate rapamycin-binding proteins.

DESCRIPTION OF THE INVENTION

This invention provides a compound of formula I which is useful as an immunosuppressive, antiinflammatory, antifungal, antiproliferative, and antineoplastic agent and useful for measuring levels of rapamycin; for isolating rapamycin-binding proteins; and detecting monoclonal antibodies specific for rapamycin or derivatives thereof, having the structure

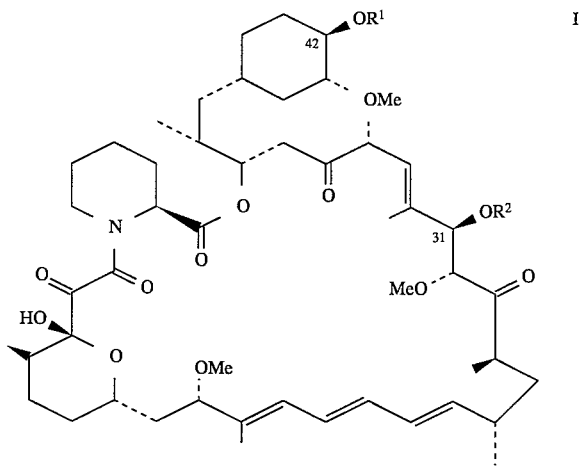

$R^1$ and $R^2$ are each, independently, hydrogen or

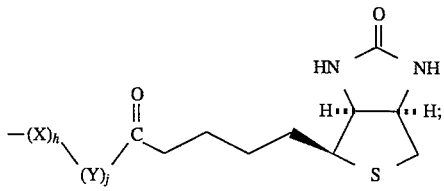

X is

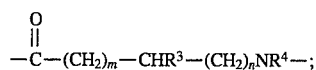

Y is

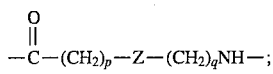

Z is —CH$_2$—, —S—S—, or

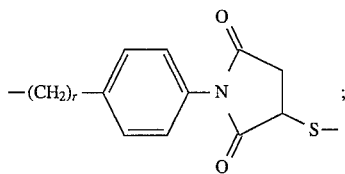

R$^3$ is hydrogen, alkyl of 1–6 carbon atoms, arylalkyl of 7–10 carbon atoms, alkenyl of 2–7 carbon atoms, alkynyl of 2–7 carbon atoms, —(CH$_2$)$_q$CO$_2$R$^5$, —(CH$_2$)$_r$NR$^6$R$^7$, carbamylalkyl of 2–3 carbon atoms, aminoalkyl of 1–4 carbon atoms, hydroxyalkyl of 1–4 carbon atoms, guanylalkyl of 2–4 carbon atoms, mercaptoalkyl of 1–4 carbon atoms, alkylthioalkyl of 2–6 carbon atoms, indolylmethyl, hydroxyphenylmethyl, imidazoylmethyl, halo, trifluoromethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —CO$_2$H;

R$^4$, R$^6$, and R$^7$ are each, independently, hydrogen, alkyl of 1–6 carbon atoms, or arylalkyl of 7–10 carbon atoms;

R$^5$ is hydrogen, alkyl of 1–6 carbon atoms, arylalkyl of 7–10 carbon atoms, alkenyl of 2–7 carbon atoms, alkynyl of 2–7 carbon atoms, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —CO$_2$H;

h=0–1;
j=0–1;
m=0–6;
n=0–6;
p=0–10;
q=0–10;
r=0–6;

with the proviso that R$^1$ and R$^2$ are not both hydrogen, or a pharmaceutically acceptable salt thereof.

When any of the compounds of this invention contain an aryl or arylalkyl moiety, it is preferred that the aryl portion is a phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl group that may be optionally mono-, di-, or tri-substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —SO$_3$H and —CO$_2$H. It is more preferred that the aryl moiety is a phenyl group that is optionally mono-, di-, or tri- substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —SO$_3$H and —CO$_2$H.

The pharmaceutically acceptable salts are those derived from such inorganic cations such as sodium, potassium, and the like; organic bases such as: mono-, di-, and trialkyl amines of 1–6 carbon atoms, per alkyl group and mono-, di-, and trihydroxyalkyl amines of 1–6 carbon atoms per alkyl group, and the like; and organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

Of these compounds, preferred members are those in which j=0; those in which R$^3$ is hydrogen or alkyl of 1–6 carbon atoms; those in which j=1 and Z is —S—S— or

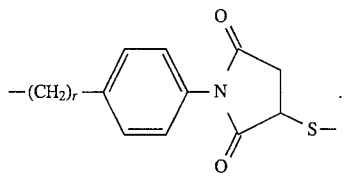

It is contemplated that when the compounds of this invention are used as an immunosuppressive or antiinflammatory agent, they can be administered in conjunction with one or more other immunoregulatory agents. Such other antirejection chemotherapeutic agents include, but are not limited to azathioprine, corticosteroids, such as prednisone and methylprednisolone, cyclophosphamide, rapamycin, cyclosporin A, FK-506, OKT-3, and ATG. By combining a compound of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23: 507 (1991)].

X and Y are linker moieties that correspond to any molecule containing a free carboxylic acid at one end and a free primary or secondary amino group on the other end. Preferred linker groups are shown as X and Y in the compound of Formula I.

The compounds of this invention can be prepared by reacting biotin with the amino group of a peptide in which the terminal carboxylic acid has been protected with a suitable protecting group, such as a t-butyl ester, in the presence of 1-(3-dimethylaminopropyl)-3-ethyl carbodiimide (DAEC), hydroxybenzotriazole (HOBT), and N-methylmorpholine. For compounds of this invention in which j=0, the same reaction is used beginning with a carboxy-protected amino acid. The carboxylic acid protecting group is then removed under standard conditions. For a t-butyl ester, trifluoroacetic acid in methylene chloride can be used.

For compounds of this invention containing biotin esters at the 42-position or at both the 31- and 42-positions, the deprotected biotin adduct is reacted with rapamycin in the presence of triethylamine, DAEC and dimethylamino pyridine (DMAP) to provide the desired biotin esters. For compounds of this invention containing biotin esters at the 31-position of rapamycin, the biotin adduct described above is reacted as described above, with rapamycin in which the 42-position is protected with a suitable protecting group, such as with a tert-butyldimethyl silyl group to give 42-O-silylated rapamycin 31-biotin ester. Deprotection of the 42-hydroxyl group provides the desired 31-biotin ester of rapamycin. The preparation of 42-O-silyl ethers of rapamycin and subsequent deprotection is described in U.S. Pat. No. 5,120,842, which is hereby incorporated by reference.

The reagents used to prepare the compounds of the invention are commercially available or can be prepared by methods that are disclosed in the literature.

This invention also covers analogous biotin esters of other rapamycins such as, but not limited to, 29-demethoxyrapamycin, [U.S. Pat. No. 4,375,464, 32-demethoxyrapamycin under C. A. nomenclature]; rapamycin derivatives in which the double bonds in the 1-, 3-, and/or 5-positions have been reduced [U.S. Pat. No. 5,023,262]; 42-oxorapamycin [U.S. Pat. No. 5,023,262]; 27-oximes of rapamycin [U.S. Pat. No. 5,023,264]; 27-hydrazones of rapamycin [U.S. Pat. No. 5,120,726]; 29-desmethylrapamycin [U.S. Pat. No. 5,093,339, 32-desmethylrapamycin under C. A. nomenclature]; 7,29-bisdesmethylrapamycin [U.S. Pat. No. 5,093,338, 7,32-desmethylrapamycin under C.A. nomenclature]; and 15-hydroxy- and 15,27 -bishydroxy-rapamycin [U.S. Pat. No. 5,102,876]. The disclosures in the above cited U.S. Patents are hereby incorporated by reference.

Immunosuppressive activity for a representative compound of this invention was evaluated in an in vitro standard pharmacological test procedure to measure the inhibition of lymphocyte proliferation (LAF).

The comitogen-induced thymocyte proliferation procedure (LAF) was used as an in vitro measure of the immunosuppressive effects of representative compounds. Briefly, cells from the thymus of normal C3H mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. For each compound evaluated, rapamycin was also evaluated for the purpose of comparison. An $IC_{50}$ was obtained for each test compound as well as for rapamycin. The results obtained for the representative compound of this invention are expressed as an $IC_{50}$ and as the percent inhibition of T-cell proliferation at various concentrations. The results are also expressed as a ratio compared to rapamycin. A positive ratio indicates immunosuppressive activity. A ratio of greater than 1 indicates that the test compound inhibited thymocyte proliferation to a greater extent than rapamycin. Calculation of the ratio is shown below.

$$\frac{IC_{50} \text{ of Rapamycin}}{IC_{50} \text{ of Test Compound}}$$

The compound of Example 3 was evaluated twice in the LAF standard pharmacological test procedure. In the first evaluation the compound of Example 3 had an $IC_{50}$ of 2.8 nM and inhibited T-cell proliferation by 46% at 1 nM, by 65% at 3 nM, by 95% at 10 nM, by 98% at 0.1 nM, and by 99% at 1 μM. In the first evaluation, rapamycin had an $IC_{50}$ of 6.7 nM. A ratio of 2.39 was obtained according to the calculation described above. In the second evaluation, the compound of Example 3 had an $IC_{50}$ of 1.3 nM and inhibited T-cell proliferation by 16% at 1 nM, by 51% at 3 nM, by 88% at 10 nM, by 94% at 0.1 nM, and by 96% at 1 μM. In the second evaluation, rapamycin had an $IC_{50}$ of 0.8 nM to provide a ratio of 0.63.

The results of a representative compound in the LAF standard pharmacological test procedure demonstrates immunosuppressive activity for the compounds of this invention. A positive ratios in the LAF test procedures indicates suppression of T-cell proliferation, thereby demonstrating the immunosuppressive activity of the compounds of this invention.

Based on the results in the standard pharmacological test procedure, the compounds of this invention are useful for inducing immunosuppression, in the treatment or prevention of transplantation rejection such as kidney, heart, liver, lung, bone marrow, pancreas (islet cells), cornea, small bowel, and skin allografts, and heart valve xenografts; in the treatment of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation, asthma, and eye uveitis.

Because the compounds of this invention are structurally similar to rapamycin and have a similar activity profile to rapamycin, the compounds of this invention also are considered to have antineoplastic, antifungal activities, and antiproliferative activities. The compounds of this invention therefore are also useful in treating solid tumors, adult T-cell leukemia/lymphoma, fungal infections, and hyperproliferative vascular diseases such as restenosis and atherosclerosis.

The compounds of this invention are particularly advantageous as therapeutic agents for the above disease states as they can be used to target the active moiety to a subpopulation of cells sensitive to rapamycin. This can be accomplished by combining the compounds of this invention with streptavidin or avidin which is conjugated to a protein, lipid, or carbohydrate molecule or fragment thereof which can bind to a molecule on the cell surface of the targeted subpopulation. Specifically targeting subpopulation of cells allows lower dosages of active moiety to be used to achieve efficacious results, thereby providing an improved therapeutic index over non-specific treatments. This technique has been used in the cancer field where antibodies coupled to toxins such as ricin, maytansinoids, or mitomycin C have been used to target the toxin, ricin, to the cells recognized by the antibody [Chari, Canc. Res. 52: 127 (1992); Hall, J. Neurosurg. 76: 1 (1992); Byers, Semin. Cell Biol. 2: 59 (1991)]. Although in some instances, in vivo administration yielded some toxicity, most probably due to the uptake of the molecules by the liver and kidney and to the premature release of ricin from the targeting molecule, some immunoconjugates showed high antigen-specific cytotoxicity for cultured human cancer cells, low systemic toxicity in mice and good pharmacobehavior (Chari et al., Canc. Res. 52: 127–131, 1992). Similarly, antibodies coupled to a radioactive moiety or other label have been used for identification of a cell type recognized by the antibody, i.e. imaging. Immunotoxins such as an anti-CD5 antibody conjugated to ricin [Byers, Semin. Cell Biol. 2: 59 (1991)] can be used to target CD5+ T-lymphocytes in vitro and are potential therapies for graft versus host disease.

In addition to being useful for inducing immunosuppression and treating the above described conditions, the compounds of this invention are also useful for measuring levels of rapamycin and derivatives thereof; for isolating rapamycin-binding proteins; and detecting monoclonal antibodies specific for rapamycin or derivatives thereof. Rapamycin derivatives as defined here are compounds containing a rapamycin nucleus, a metabolite of rapamycin, or a ring opened rapamycin (such as secorapamycin, described in U.S. Pat. No. 5,252,579 which is hereby incorporated by reference), in which one or more of the hydroxyl groups has been esterified into a carboxylic ester, a carbamate, a sulfonate ester, an amide, or the like, or one or more of the ketones has been reduced to a hydroxyl group, or one or more of the double bonds has been reduced, or one ketones has been converted to an oxime or a hydrazone. Other rapamycin derivatives for which the compounds of this invention can be used for measuring levels of or generating antibodies to will be apparent to one skilled in the art based on this disclosure.

Although many variations of the immunoassay can be used (antigen capture, antibody capture, competitive inhibition, or two antibody immunoassay), a basic competitive inhibition immunoassay can be performed as follows: Antibody specific for a ligand is usually bound to a matrix. A solution is applied to decrease nonspecific binding of the ligand to the matrix. After rinsing the excess away, the antibody coupled matrix may be treated in some cases so it can be stored. In a competitive inhibition assay, the ligand standard curve is made and added with the rap amycin-biotin ester to compete for binding to the rapamycin-specific antibody. If necessary, the excess is removed. A detector molecule coupled to streptavidin or avidin is added which binds to the rapamycin-biotin ester present. The detector molecule is detected by the standard methods used by one skilled in the art. However, there are many strategies which can be used for development of an immunoassay as practiced by one skilled in the art, including EMIT, VISTA, MEIA, RIA, FPIA, dipstick, ELISA, as well as assays based on chemiluminescence. Similar methods can be used to make a receptor based assay.

The following is an example of the use of the compounds of this invention to detect antibodies specific for rapamycin or a derivative thereof, using an ELISA format. The compound of Example 3 was used as a representative compound of this invention. Microtiter plates (Immulon I) were coated overnight with 100 µl of goat anti-mouse antibody (10 µg/ml in 10 mM potassium phosphate buffer, pH 7.2) at 4° C. The plates were flicked and blocked with 100 µl of 1% bovine sera albumin in phosphate buffered saline (PBS) overnight at 4° C. After flicking and washing the plates thrice with 0.2× PBS containing 0.02% Triton X-100 and 0.004% thimerosal, 100 µl of each hybridoma supernatant was added to a well and incubated at room temperature for overnight. After flicking and washing the plates thrice with 0.2×PBS containing 0.02% Triton X-100 and 0.004% thimerosal, the compound of Example 3 (100 µl, 0.17 µM) was added and incubated for 1 hour at 4° C. After flicking and washing the plates thrice with 0.2×PBS containing 0.02% Triton X-100 and 0.004% thimerosal, strepavidin or avidin conjugated to horseradish peroxidase (100 µl, 0.2 µg/ml) was added and incubated at room temperature for 1 hour in the dark. After flicking and washing the plates thrice with 0.2×PBS containing 0.02% Triton X-100 and 0.004% thimerosal, TMB substrate and $H_2O_2$ was added and the plates were incubated covered for 30 min. at room temperature in the dark. The optical density was read on a spectrophotometer at 450 nm. An optical density reading of 0.25–3 indicates specific antibody binding. The results in Table 1 show that the hybridoma from well P4G1 is positive for binding to the compound of Example 3, and is therefore specific for rapamycin or a derivative thereof.

TABLE 1

Screening for Monoclonal Antibodies Specific for Rapamycin or a Derivative Thereof

| WELL | OPTICAL DENSITY |
| --- | --- |
| P3H4 | 0.120 |
| P3H5 | 0.105 |
| P4G1 | 1.940 |

The hybridoma cell line in P4G1 was cloned by limiting dilution and is designated as hybridoma cell line, RAP-42-OVAF$_2$#1hc-. The hybridoma cell line, RAP-42-OVAF$_2$#1hc, was deposited under the terms of the Budapest Treaty with the American Type Culture Collection (ATCC) of 12301 Parklawn Drive, Rockville, Md., 20852, U.S.A., on Mar. 10, 1994, and was granted accession number HB 11568. In a Fluorescent Polarization Immunoassay (FPIA), rapamycin 42-ester with succinic acid conjugate with 5-glycinylfluoresceinamine was used as a tracer at a concentration of 10 nM and showed a polarization of 77 mP in 100 mM sodium phosphate pH 7.5. After addition of an excess of FKBP12, the polarization measured 195 mP whereas the addition of excess of RAP-42-OVAF2#1MoAb yielded 84 mP. The ring opened non-enzymatically transformed product of the above tracer (secorapamycin 42-ester with succinic acid conjugate with 5-fluoresceinamine) was isolated on TLC plate (50:chloroform:4 methanol:0.5 acetic acid; migrated slowest of three components). The slowest migrating material, termed A3, had a background reading of 75 mP and a reading of 178 mP in presence of RAP-42-OVAF2#1MoAb. Background levels were observed in the presence of FKBP12 (79 mP). Competition of the binding between the antibody and A3 tracer with rapamycin or secorapamycin at 3 min was 155 mP and 105 mP, respectively and after 38 min. gives 121 mP and 89 mP, respectively. The ring opened rapamycin-specific antibody, designated as RAP-42-OVAF$_2$#1MoAb, was isolated and purified using conventional methodology.

When immunosuppressive agents such as rapamycin are administered, it is useful to accurately determine levels of the immunosuppressive agent present in the patient to allow the dosage to be adjusted to maintain adequate immunosuppression without causing undesirable effects from overimmunosuppression. The compounds of this invention can be used in an immunoassay or receptor based assay as the first part of the detection molecule by mixing the test sample or the rapamycin standard with biotin ester of rapamycin and allowing them to compete for binding to the antibody or receptor. After rinsing with an appropriate wash buffer, a detection molecule consisting of streptavidin or avidin conjugated to an enzyme, fluorescent or chemiluminescent molecule, or radioactive moiety can be used.

The following is an example of the use of the compounds of this invention in a competitive inhibition assay for determining levels of rapamycin with an ELISA format using an antibody specific for rapamycin or a derivative thereof. The compound of Example 3 was used as a representative compound of this invention. Microtiter plates (Immulon I) were coated overnight with 100 µl of goat anti-mouse antibody (10 µg/ml in 10 mM potassium phosphate buffer, pH 7.2) at 4° C. The plates were flicked and blocked with 100 µl of 1% bovine sera albumin in phosphate buffered saline overnight at 4° C. After flicking and washing the plates three times with 0.2×PBS containing 0.02% Triton X-100 and 0.004% thimerosal, rapamycin specific antibody (100 µl of 1 µg/ml) was added to each well and incubated at room temperature for 1–4 hour. After flicking and washing the plates three times with 0.2×PBS containing 0.02% Triton X-100 and 0.004% thimerosal, the compound of Example 3 (100 µl, 0.17 µM) in the presence or absence of various concentrations of rapamycin was added and incubated for 1 hour. After flicking and washing the plates three times with 0.2×PBS containing 0.02% Triton X-100 and 0.004% thimerosal, streptavidin conjugated to horseradish peroxidase (100 µl, 0.2 µg/ml) was incubated at room temperature for 1 hour in the dark. After flicking and washing the plates three times with 0.2×PBS containing 0.02% Triton X-100 and 0.004% thimerosal, OPD substrate was added and the plates were incubated covered for 15 min. at room temperature in the dark. The optical density was read on a spectrophotometer at 492 nm. Table 2 shows the percent inhibition of binding of the compound of Example 3 by various concentrations of rapamycin. From these data, a standard curve can be generated from which the concentration of rapamycin in a sample can be determined.

TABLE 2

| RAPAMYCIN CONCENTRATION | OD | % INHIBITION |
|---|---|---|
| 5 µM | .705 | 67.6 |
| 0.5 µM | 1.419 | 30.1 |
| 0.05 µM | 1.842 | 7.8 |
| 0.005 µM | 1.866 | 6.6 |
| 0 µM | 1.992 | 0 |

The following is an example of the use of the compounds of this invention in a receptor based assay to measure rapamycin levels using a rapamycin-binding protein and the compound of Example 3 as the ligand. Wells of microtiter plates were coated with 0.5 µg/well of the fusion protein, glutathione S-transferase-FK506 binding protein (GST-FKBP), in 100 µl of 0.02M HEPES buffer, pH 7.4. Plates were incubated overnight at 4° C. Plates were washed 3 × with HEPES buffer. Well surfaces were blocked by the addition of 1% bovine serum albumin fraction V (BSA) in HEPES buffer (300 µl/ml). Plates were incubated for 1 hour at ambient temperature. Plates were washed three times. Various concentrations of rapamycin were added to the compound of Example 3 (50 ng/ml) and 100 µl of the solutions were added to wells in triplicate. After incubation of the plates at ambient temperature followed by washing the plates with HEPES buffer, 100 µl of diluted avidin-horseradish peroxidase conjugate was added to each well. After incubation for 1 hour at ambient temperature and washing five times, 100 µl of tetramethylbenzidine substrate was added to each well. The plates were incubated for 30 minutes in the dark at ambient temperature. The reactions were stopped and the optical density was read at 450 nm. The results are shown in Table 3. From these data, a standard curve can be generated from which the concentration of rapamycin in a sample can be determined.

TABLE 3

Rapamycin Competitive Binding Assay using the Compound of Example 3

| Rapamycin Concentration (ng/ml) | Optical Density |
|---|---|
| 200 | 0.2177 |
| 100 | 0.2433 |
| 50 | 0.3573 |
| 25 | 0.7473 |
| 12.5 | 1.3913 |
| 6.25 | 2.0557 |
| 3.125 | 2.3040 |
| 1.5625 | 2.6160 |

Similarly, assays for determining concentrations of rapamycin can be developed based on chemiluminescence, fluorescence, or a radiolabeled entity (conjugated to streptavidin or avidin) using the compounds of this invention.

The compounds of this invention can also be used in a solid matrix type assay to determine rapamycin concentrations, identify and isolate rapamycin-binding proteins, and identify antibodies specific for rapamycin or a derivative thereof. Thus, the compounds of this invention can be bound to a streptavidin or avidin conjugated matrix and used in a dipstick type immunoassay or can be used in an affinity column that will detect rapamycin, rapamycin-binding proteins, and antibodies specific to rapamycin or a derivative thereof.

The following procedure illustrates the binding of a ring opened rapamycin specific antibody to the compound of Example 3 to streptavidin bound conjugated to a solid matrix. Streptavidin (100 µg/ml 10 mM sodium acetate, pH 4.5, 0.05% P20) was conjugated using the BIAcore's standard protocol based on EDC and NHS to the solid matrix used in a BIAcore. The compound of Example 3 (2.5 mM) was injected over the sample and 115 resonance units bound. The monoclonal antibody, RAP-42-OVAF$_2$#1MoAb, at 2.5 µg/ml was then injected and 1932 RU were bound. The kinetics of association and dissociation were determined for each concentration of antibody tested (0.625, 1.25, 2.5, 5.0, 10.0 ug/ml). These data show that the compound of Example 3, even when bound to a streptavidin conjugated matrix was accessible to binding by a rapamycin-specific antibody and the interaction could be characterized. Similar procedures can be used to bind a rapamycin-binding protein to rapamycin—biotin—streptavidin or avidin conjugated matrix. Compounds of this invention can also be used in association with a streptavidin or avidin matrix for the isolation of novel binding proteins, as practiced by one skilled in the art. Two strategies are listed below as examples. Rapamycin-biotin esters can be used to isolate binding proteins of rapamycin or of rapamycin-FKBP complex by one of the following methods. In the first set of approaches, tissue or cell lysates containing the appropriate protease inhibitors are incubated with a rapamycin-biotin ester or FKBP-rapamycin-biotin ester complex for a sufficient time to allow binding. The solution is incubated with a streptavidin or avidin conjugated resin for an appropriate time and at a relevant temperature. Various buffers can be used to rinse the proteins which are nonspecifically bound. Proteins are released by the addition of additional buffers which disrupt the bond between the rapamycin-biotin ester and the binding proteins. In the second set of approaches, an affinity column is made in which a rapamycin-biotin ester is bound to a streptavidin coupled matrix. Cell or tissue lysates containing the appropriate protease inhibitors is mixed or poured and incubated with the resin to allow binding of binding proteins. After rinsing the column with the appropriate buffers to remove unbound or weakly bound proteins, appropriate buffers are used to elute the rapamycin-binding proteins.

The above procedures demonstrate that the compounds of this invention are useful for developing an assay for measuring levels of rapamycin; for isolating rapamycin-binding proteins; and detecting monoclonal antibodies specific for rapamycin or derivatives thereof. The above assays also allow the measurement of rapamycin to be performed on multiple samples at one time. Based on the procedures described above, the compounds of this invention can also be used to identify the metabolites, binding proteins, and effector molecules of rapamycin or structurally related molecules by affinity chromatography or by precipitation using streptavidin or avidin conjugated to a larger molecule.

The following examples illustrate the preparation of a representative compound of this invention.

EXAMPLE 1 tert-Butylgylcylbiotin

To a solution of biotin (0.83 g, 3.4 mmol) in 60 mL of DMF was added glycine t-butyl ester hydrochloride (0.57 g, 3.4 mmol), N-methylmorpholine (0.92 mL, 8.36 mmol), 1-hydroxybenzothiazole (0.61 g, 3.99 mmol) and 1-(3-Dimethylaminopropyl)-3-ethylcarbo-diimide hydrochloride (0.65 g, 3.4 mmol). The reaction mixture was stirred at room temperature for 7 days. The DMF was concentrated, ethyl acetate was added, and the organic layer was washed with water, 0.5N HCl, saturated sodium bicarbonate, and brine. The ethyl acetate layer was dried ($MgSO_4$) and concentrated to yield the title compound as a white solid which was primarily one spot on TLC (0.611 g, 1.71 mmol, 50%). Mass spec $[M+H]^+$ at m/z 358.

EXAMPLE 2

Glycylbiotin

To a solution of tert-butylglycylbiotin (0.271 g, 0.758 mmol) in $CH_2Cl_2$ (0.5 mL) was added 0.5 mL trifluoroacetic acid. The reaction mixture was stirred at room temperature for 2 h, concentrated, and triturated with anhydrous diethyl ether. The off-white precipitate was collected to yield 0.209 g (0.694 mmol, 92%) of the title compound. Mass spec $[M+H]^+$ at m/z 302.

EXAMPLE 3

Rapamycin 42-ester with glycylbiotin

To a solution of glycylbiotin (0.65 g, 2.16 mmol) in 1-methylpyrrolidinone (5 mL) was added 6 mL of $CH_2Cl_2$, causing a precipitate to form which persisted even after the addition of 0.33 mL (2.36 mmol) of triethylamine. To this heterogeneous solution was added 2 g (2.19 mmol) of rapamycin, 0.43 g (2.24 mmol) of 1-(3-dimethylaminopropyl)-3-ethylcarbodiimide hydrochloride, and 30 mg (2.46 mmol) of DMAP. After several hours, the reaction mixture became homogenous, and was stirred an additional four days. A large excess of ethyl acetate was added and the organic layer was washed with water, 0.5N HCl, saturated sodium bicarbonate, and brine. The organic layer was dried ($MgSO_4$) and concentrated. The light yellow foam was triturated with hot anhydrous diethyl ether to yield 1.2 g of impure title compound as a light yellow solid. A portion (0.5 g) of this material was flash chromatographed in 5% MeOH/$CHCl_3$, and triturated again in hot ether to yield 87 mg of the title compound contaminated with a small amount of rapamycin. This material was rechromatographed (gradient 0–5% MeOH/$CHCl_3$), and triturated a final time with ether to yield 34 mg (0.028 mmol) of pure title compound as a white solid. Mass spec, negative FAB $M^-$ at m/z 1196.

The following example illustrates the formulation and dosage requirements for the compounds of this invention, when they are used as pharmacological agents.

EXAMPLE 4

When used as pharmacological agents, as described above, the compounds of this invention can be formulated neat or with a pharmaceutical carder to a mammal in need thereof. The pharmaceutical carder may be solid or liquid.

A solid carder can include one or more substances which may also act as flavoring agents, lubricants, solubilizers, suspending agents, fillers, glidants, compression aids, binders or tablet-disintegrating agents; it can also be an encapsulating material. In powders, the carder is a finely divided solid which is in admixture with the finely divided active ingredient. In tablets, the active ingredient is mixed with a carder having the necessary compression properties in suitable proportions and compacted in the shape and size desired. The powders and tablets preferably contain up to 99% of the active ingredient. Suitable solid carders include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carders are used in preparing solutions, suspensions, emulsions, syrups, elixirs and pressurized compositions. The active ingredient can be dissolved or suspended in a pharmaceutically acceptable liquid carder such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carder can also be an oily ester such as ethyl oleate and isopropyl myristate. Sterile liquid carders are useful in sterile liquid form compositions for parenteral administration. The liquid carder for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carder that is inert to the active compound, is non toxic to the skin, and allows delivery of the agent for systemic absorption into the blood stream via the skin. The carder may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane coveting a reservoir containing the active ingredient with or without a carder, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 μg/kg–100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is subdivided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

What is claimed is:

1. A compound of the structure

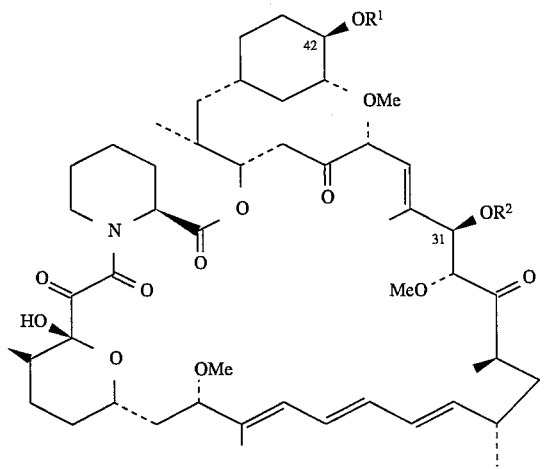

I $R^1$ and $R^2$ are each, independently, hydrogen or

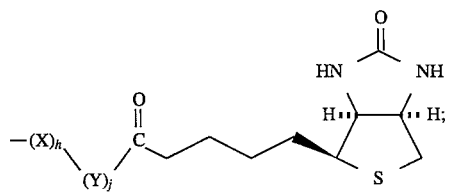

X is

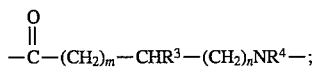

Y is

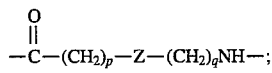

Z is $-CH_2-$, $-S-S-$, or

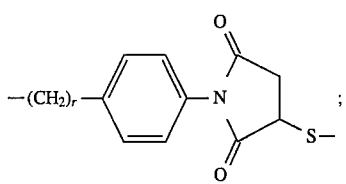

$R^3$ is hydrogen, alkyl of 1–6 carbon atoms, arylalkyl of 7–10 carbon atoms, alkenyl of 2–7 carbon atoms, alkynyl of 2–7 carbon atoms, $-(CH_2)_qCO_2R^5$, $-(CH_2)_rNR^6R^7$, carbamylalkyl of 2–3 carbon atoms, aminoalkyl of 1–4 carbon atoms, hydroxyalkyl of 1–4 carbon atoms, guanylalkyl of 2–4 carbon atoms, mercaptoalkyl of 1–4 carbon atoms, alkylthioalkyl of 2–6 carbon atoms, indolylmethyl, hydroxyphenylmethyl, imidazoylmethyl, halo, trifluoromethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or $-CO_2H$;

$R^4$, $R^6$, and $R^7$ are each, independently, hydrogen, alkyl of 1–6 carbon atoms, or arylalkyl of 7–10 carbon atoms;

$R^5$ is hydrogen, alkyl of 1–6 carbon atoms, arylalkyl of 7–10 carbon atoms, alkenyl of 2–7 carbon atoms, alkynyl of 2–7 carbon atoms, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or $-CO_2H$;

h=0–1;
j=0–1;
m=0–6;
n=0–6;
p=0–10;
q=0–10;
r=0–6;

with the proviso that $R^1$ and $R^2$ are not both hydrogen, or a pharmaceutically acceptable salt thereof.

2. The compound according to claim 1 wherein j=0 or a pharmaceutically acceptable salt thereof.

3. The compound according to claim 1 wherein $R^3$ is hydrogen or alkyl of 1–6 carbon atoms or a pharmaceutically acceptable salt thereof.

4. The compound according to claim 1 wherein j=1 and Z is $-S-S-$ or

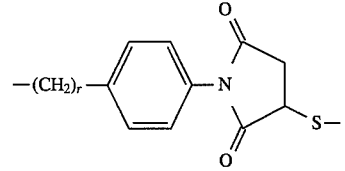

or a pharmaceutically acceptable salt thereof.

5. A compound according to claim 1 which is rapamycin 42-ester with glycylbiotin or a pharmaceutically acceptable salt thereof.

6. A method of inducing immunosuppression in a mammal in need thereof which comprises administering to said mammal an immunosuppressive amount of a compound of the structure R¹ and R² are each, independently, hydrogen or $$-(X)_h\diagdown_{(Y)_j}\!\!\!\overset{O}{\underset{}{\overset{\|}{C}}}\!\!\!-(CH_2)_4-\overset{H}{\underset{}{\cdots}}\!\!\overset{}{\underset{S}{\bigcirc}}\!\!\overset{H}{\underset{}{\cdots}}\!\!-\!\!\begin{array}{c}HN\overset{O}{\underset{}{\overset{\|}{C}}}NH\end{array}$$

X is $$-\overset{O}{\underset{}{\overset{\|}{C}}}-(CH_2)_m-CHR^3-(CH_2)_n NR^4-;$$

Y is $$-\overset{O}{\underset{}{\overset{\|}{C}}}-(CH_2)_p-Z-(CH_2)_q NH-;$$

Z is —CH₂—, —S—S—, or $$-(CH_2)_r-\!\!\!\bigcirc\!\!\!-N\!\!\bigcirc\!\!\!-S-\ ;$$

R³ is hydrogen, alkyl of 1–6 carbon atoms, arylalkyl of 7–10 carbon atoms, alkenyl of 2–7 carbon atoms, alkynyl of 2–7 carbon atoms, —(CH₂)$_q$CO₂R⁵, —(CH₂)$_r$NR⁶R⁷, carbamylalkyl of 2–3 carbon atoms, aminoalkyl of 1–4 carbon atoms, hydroxyalkyl of 1–4 carbon atoms, guanylalkyl of 2–4 carbon atoms, mercaptoalkyl of 1–4 carbon atoms, alkylthioalkyl of 2–6 carbon atoms, indolylmethyl, hydroxyphenylmethyl, imidazoylmethyl, halo, trifluoromethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —CO₂H;

R⁴, R⁶, and R⁷ are each, independently, hydrogen, alkyl of 1–6 carbon atoms, or arylalkyl of 7–10 carbon atoms;

R⁵ is hydrogen, alkyl of 1–6 carbon atoms, arylalkyl of 7–10 carbon atoms, alkenyl of 2–7 carbon atoms, alkynyl of 2–7 carbon atoms, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —CO₂H;

h=0–1;
j=0–1;
m=0–6;
n=0–6;
p=0–10;
q=0–10;
r=0–6;

with the proviso that R¹ and R² are not both hydrogen, or a pharmaceutically acceptable salt thereof.

7. A pharmaceutical composition which comprises, a compound of the structure

R¹ and R² are each, independently, hydrogen or

X is $$-\overset{O}{\underset{}{\overset{\|}{C}}}-(CH_2)_m-CHR^3-(CH_2)_n NR^4-;$$

Y is $$-\overset{O}{\underset{}{\overset{\|}{C}}}-(CH_2)_p-Z-(CH_2)_q NH-;$$

Z is —CH₂—, —S—S—, or

R³ is hydrogen, alkyl of 1–6 carbon atoms, arylalkyl of 7–10 carbon atoms, alkenyl of 2–7 carbon atoms, alkynyl of 2–7 carbon atoms, $-(CH_2)_q CO_2 R^5$, $-(CH_2)_r NR^6 R^7$, carbamylalkyl of 2–3 carbon atoms, aminoalkyl of 1–4 carbon atoms, hydroxyalkyl of 1–4 carbon atoms, guanylalkyl of 2–4 carbon atoms, mercaptoalkyl of 1–4 carbon atoms, alkylthioalkyl of 2–6 carbon atoms, indolylmethyl, hydroxyphenylmethyl, imidazoylmethyl, halo, trifluoromethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or $-CO_2 H$;

$R^4$, $R^6$, and $R^7$ are each, independently, hydrogen, alkyl of 1–6 carbon atoms, or arylalkyl of 7–10 carbon atoms;

$R^5$ is hydrogen, alkyl of 1–6 carbon atoms, arylalkyl of 7–10 carbon atoms, alkenyl of 2–7 carbon atoms, alkynyl of 2–7 carbon atoms, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or $-CO_2 H$;

h=0–1;
j=0–1;
m=0–6;
n=0–6;
p=0–10;
q=0–10;
r=0–6;

with the proviso that $R^1$ and $R^2$ are not both hydrogen, or a pharmaceutically acceptable salt thereof, and a pharmaceutical carrier.

\* \* \* \* \*